United States Patent
Akase et al.

(10) Patent No.: US 11,231,432 B2
(45) Date of Patent: Jan. 25, 2022

(54) AUTOMATIC ANALYSIS DEVICE AND AUTOMATIC ANALYSIS METHOD

(71) Applicant: HITACHI HIGH-TECH CORPORATION, Tokyo (JP)

(72) Inventors: Hiroki Akase, Tokyo (JP); Masahiko Iijima, Tokyo (JP); Chie Yabutani, Tokyo (JP); Takanori Sawada, Tokyo (JP); Rei Konishi, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 15 days.

(21) Appl. No.: 16/488,182

(22) PCT Filed: Feb. 27, 2018

(86) PCT No.: PCT/JP2018/007335
§ 371 (c)(1),
(2) Date: Aug. 22, 2019

(87) PCT Pub. No.: WO2018/163917
PCT Pub. Date: Sep. 13, 2018

(65) Prior Publication Data
US 2019/0369131 A1  Dec. 5, 2019

(30) Foreign Application Priority Data
Mar. 8, 2017 (JP) .............................. JP2017-044317

(51) Int. Cl.
*G01N 35/00* (2006.01)
*G01N 35/10* (2006.01)

(52) U.S. Cl.
CPC ..... *G01N 35/1002* (2013.01); *G01N 35/1011* (2013.01)

(58) Field of Classification Search
CPC ........... G01N 35/1002; G01N 35/1011; G01N 33/4905
See application file for complete search history.

(56) References Cited

U.S. PATENT DOCUMENTS 5,919,706 A * 7/1999 Tajima ................. G01F 23/292
422/106
6,143,578 A * 11/2000 Bendele ................ B03C 1/0332
209/214

(Continued)

FOREIGN PATENT DOCUMENTS

| CN | 104854459 A | 8/2015 |
|---|---|---|
| EP | 2937700 A1 | 10/2015 |

(Continued)

OTHER PUBLICATIONS

Translation of WO2016/136377 (Year: 2016).*
Translation of JP2009145143 (Year: 2009).*

*Primary Examiner* — Samuel P Siefke
(74) *Attorney, Agent, or Firm* — Miles & Stockbridge, P.C.

(57) ABSTRACT

Addressing the problem of preventing contamination, the present invention is characterized by being provided with a reagent nozzle (H) for discharging a reagent (M1) at a predetermined discharge pressure to a reaction vessel (V) in which a specimen (M2) is accommodated, a control unit for controlling the horizontal position of the reagent nozzle (H) in accordance with the liquid amount of the reagent (M1) and the viscosity of the reagent (M1), a dispensing unit for dispensing the reagent (M1) into the reaction vessel (V), and a photometer for detecting light radiated to a mixture of the specimen (M2) and the reagent (M1), the control unit setting the horizontal position of the reagent nozzle (H) to the center position of the reaction vessel (V) when the liquid amount of the reagent (M1) is greater than the amount of the (Continued)

specimen (M2) and the viscosity of the reagent (M1) is equal to the viscosity of the specimen (M2) or lower than the viscosity of the specimen (M2).

9 Claims, 12 Drawing Sheets

(56) References Cited

U.S. PATENT DOCUMENTS

| | | | | |
|---|---|---|---|---|
| 6,764,859 | B1* | 7/2004 | Kreuwel | C12Q 1/6806 436/178 |
| 2005/0074897 | A1* | 4/2005 | Jacobs | G01N 1/40 436/175 |
| 2015/0316570 | A1 | 11/2015 | Yoshikawa et al. | |

FOREIGN PATENT DOCUMENTS

| | | |
|---|---|---|
| JP | 2008164480 A | 7/2008 |
| JP | 2009145143 A | 7/2009 |
| JP | 20105803 A | 1/2010 |
| JP | 2012093311 A | 5/2012 |
| JP | 2015215367 A | 12/2015 |
| JP | 2016217921 A | 12/2016 |
| WO | 2014097973 A1 | 6/2014 |
| WO | 2015079829 A1 | 6/2015 |
| WO | 2016136377 A1 | 9/2016 |

\* cited by examiner

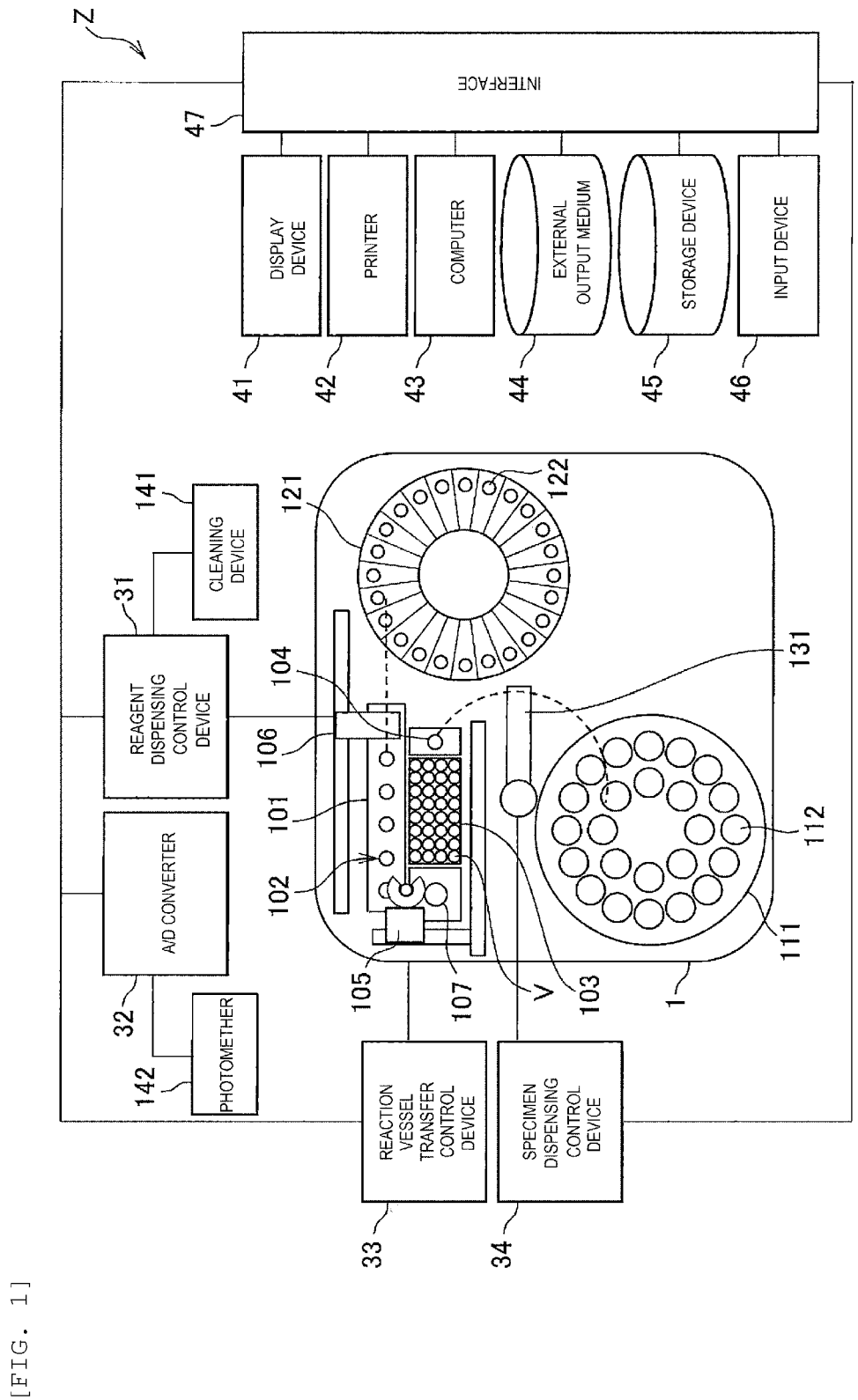
[FIG. 1]

[FIG. 2]
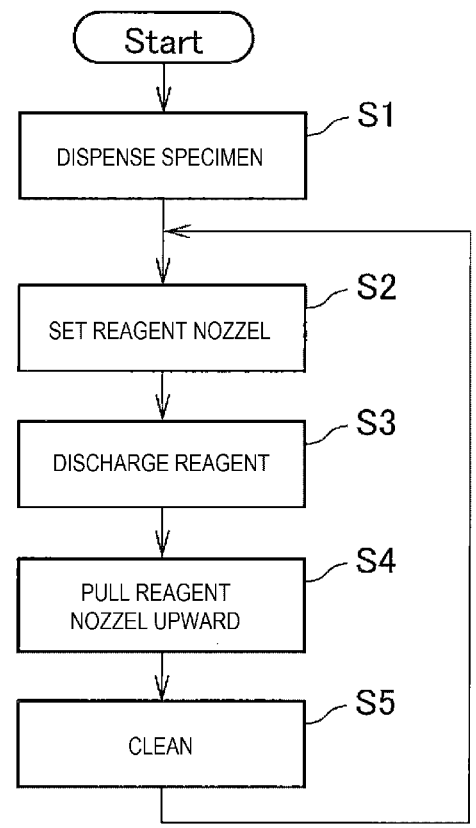

[FIG. 3]
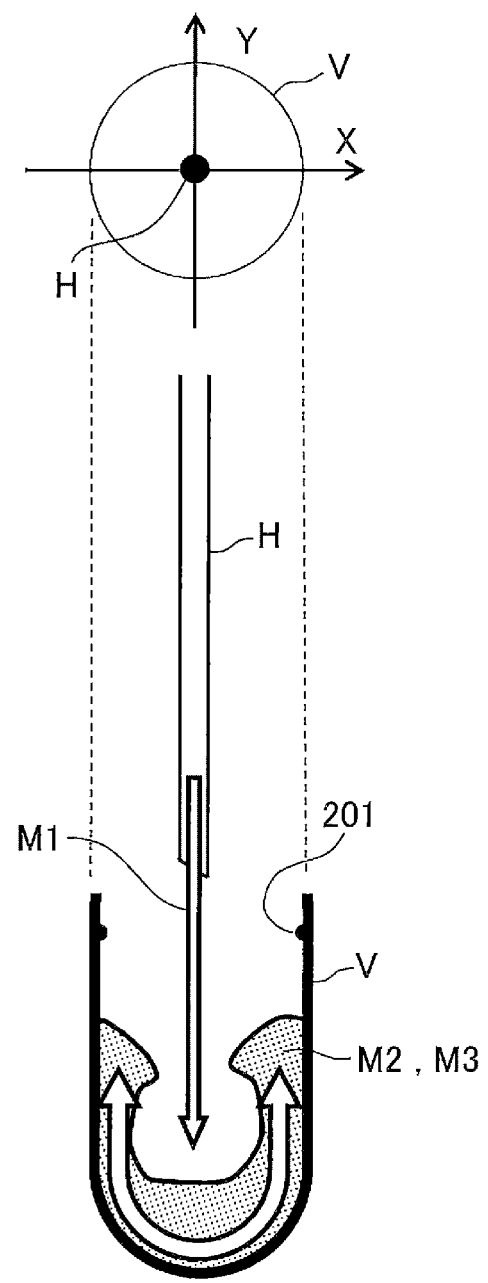

[FIG. 4]
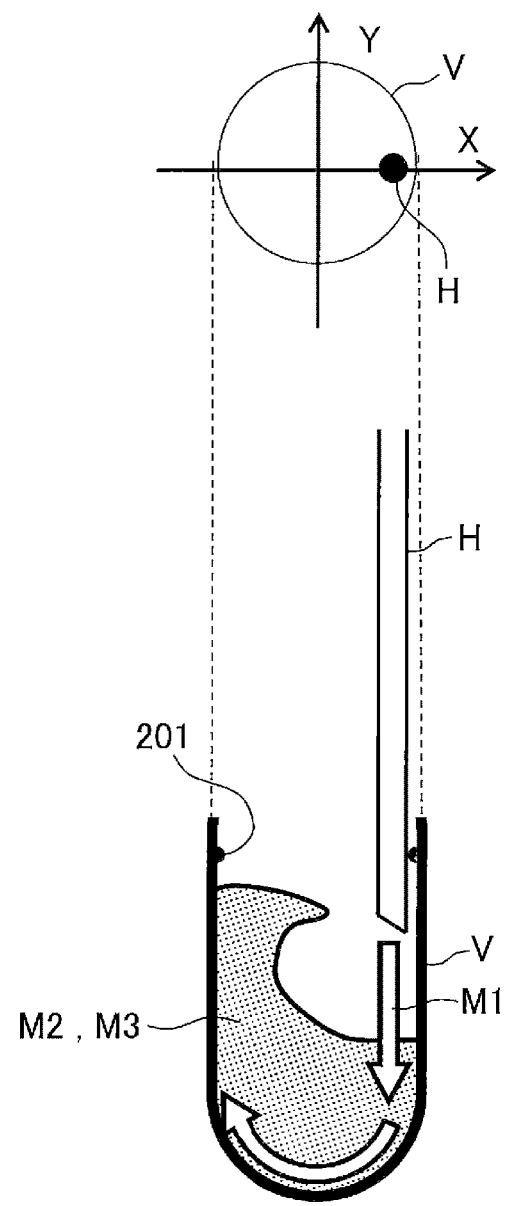

[FIG. 5]

| ITEM | VOLUME OF SPECIMEN M2 | VOLUME OF REAGENT M1 | VISCOSITY OF REAGENT M1 |
|---|---|---|---|
| A | 1 | 2 | LOW (EQUAL) |
| B | 2 | 1 | HIGH |
| C | 2 | 1 | LOW (EQUAL) |
| D | 1 | 2 | HIGH |

[FIG. 6]

| | VISCOSITY OF REAGENT M1 | | VOLUME OF REAGENT M1 | |
|---|---|---|---|---|
| | LOW | HIGH | LESS | MORE |
| AIR BUBBLE GENERATION LIKELIHOOD | LARGE | SMALL | SMALL | LARGE |
| LIFT HEIGHT | HIGH | LOW | LOW | HIGH |
| STIRRING EFFICIENCY | GOOD | BAD | BAD | GOOD |
| ITEM | A, C | B, D | B, C | A, D |

[FIG. 7]

| | NOZZEL POSITION | | NOZZEL HEIGHT | |
|---|---|---|---|---|
| | MIDDLE | END | UPPER | LOWER |
| AIR BUBBLE GENERATION LIKELIHOOD | LARGE | SMALL | LARGE | SMALL |
| LIFT HEIGHT | LOW | HIGH | LOW | HIGH |
| STIRRING EFFICIENCY | BAD | GOOD | BAD | GOOD |

[FIG. 8]
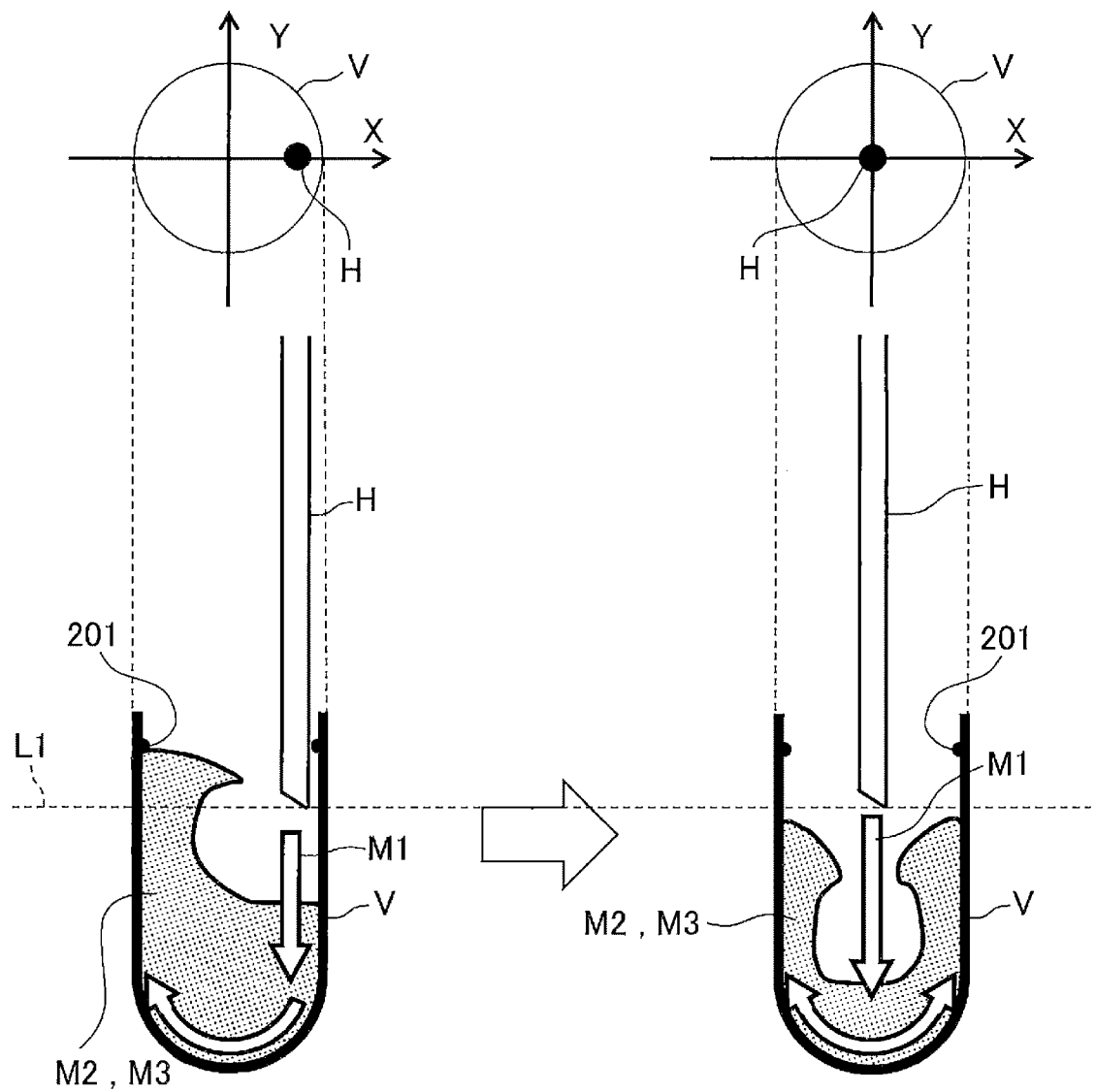

[FIG. 9]
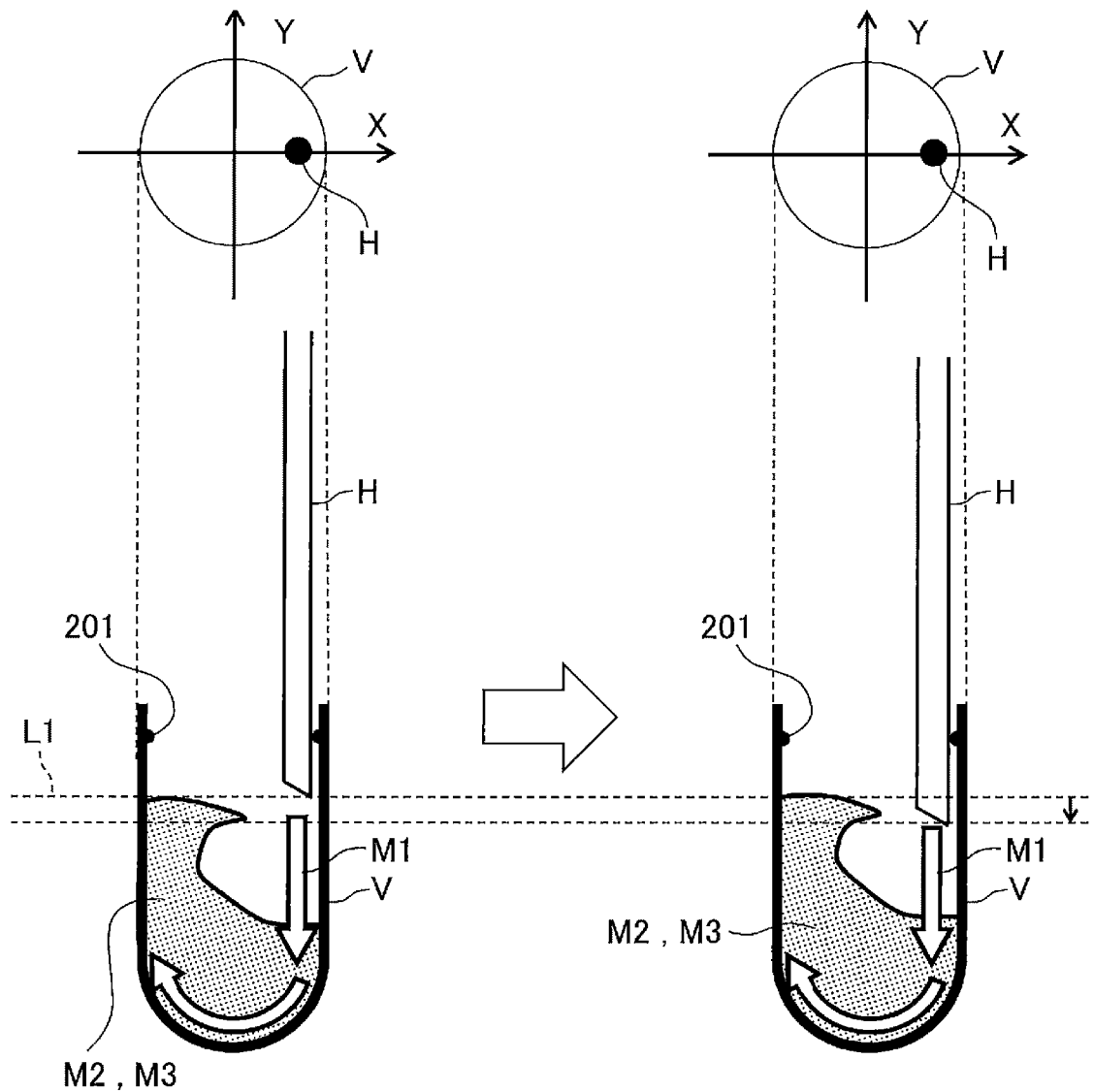

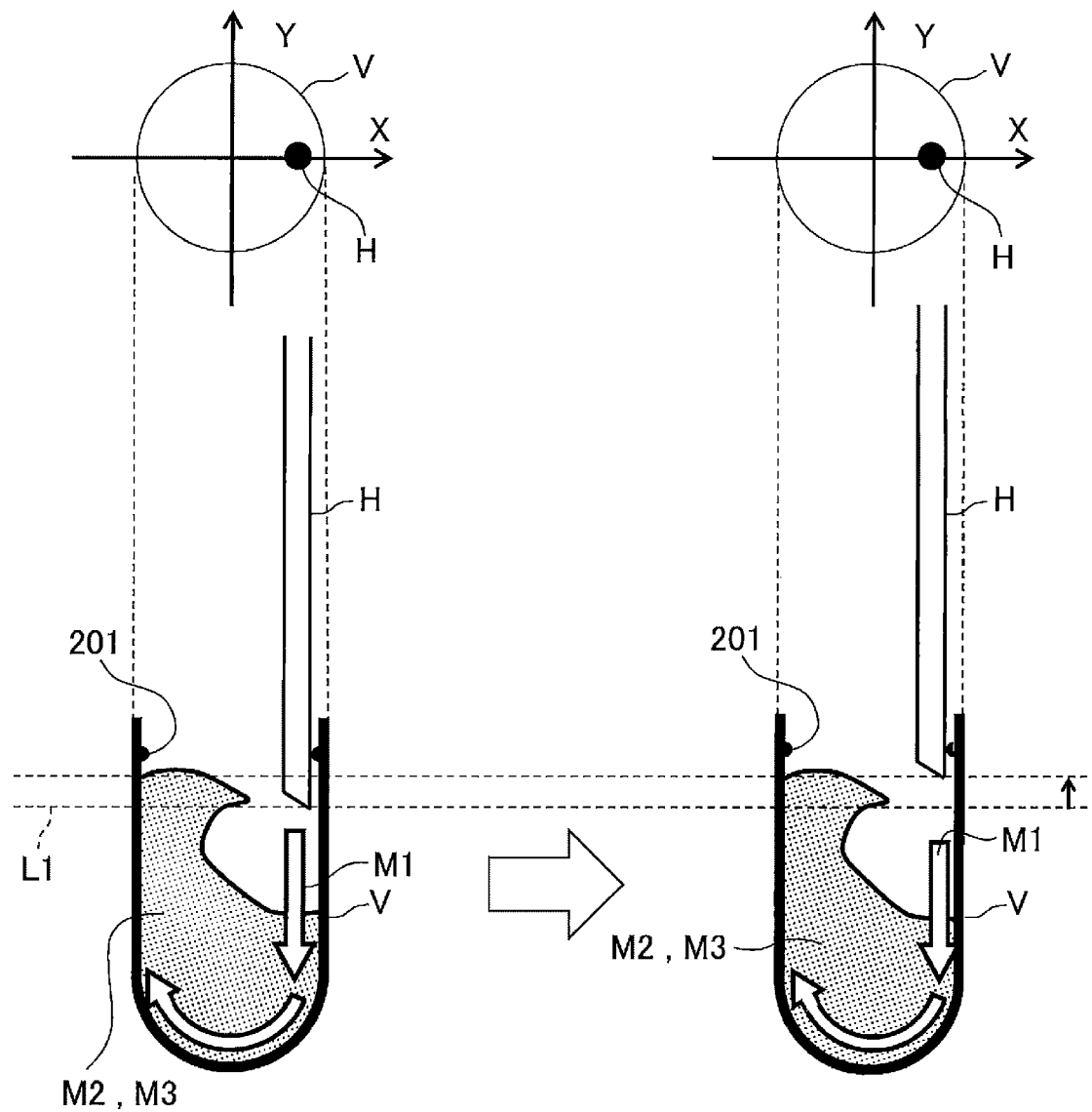
[FIG. 10]

[FIG. 11]
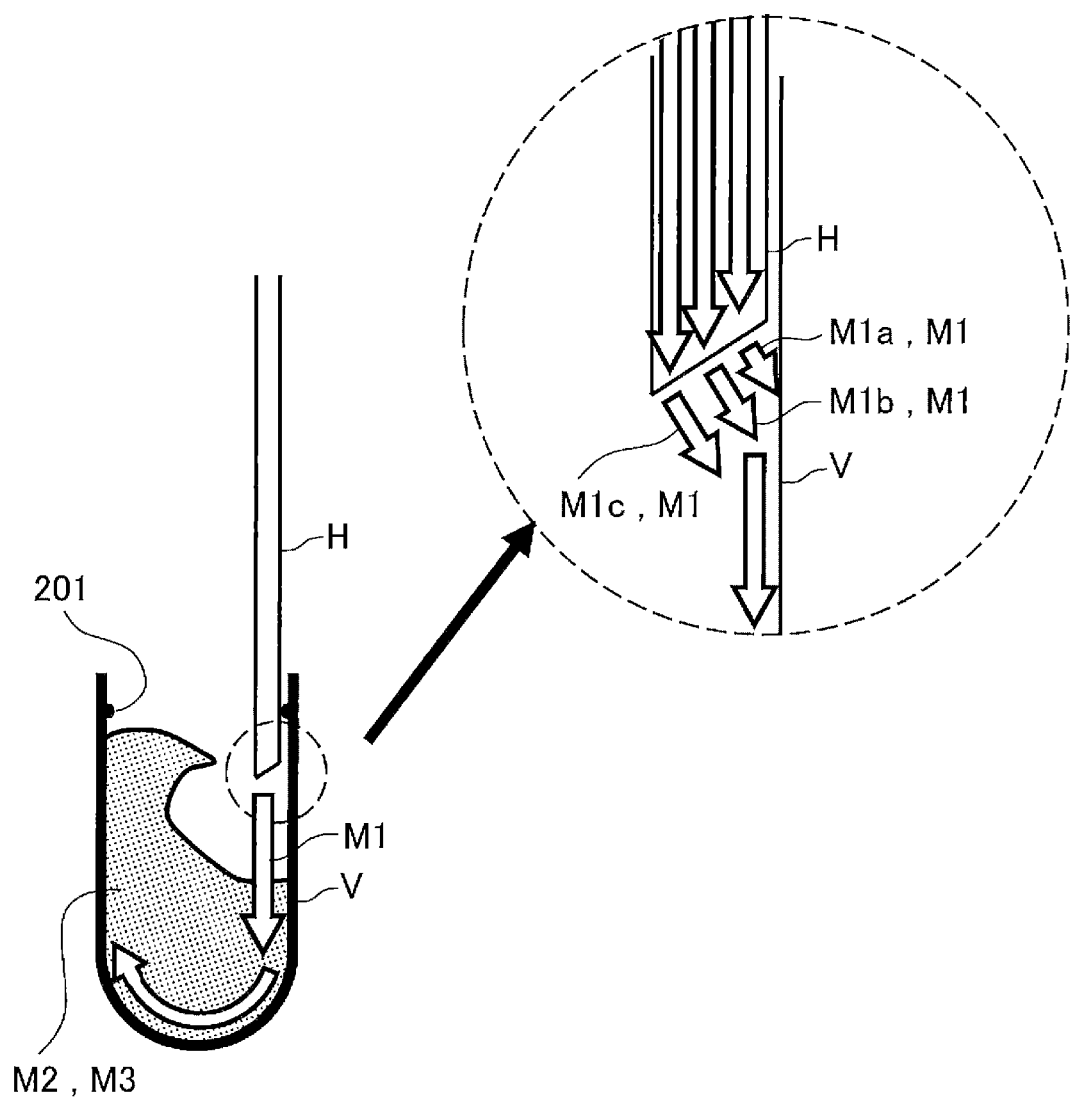

[FIG. 12]
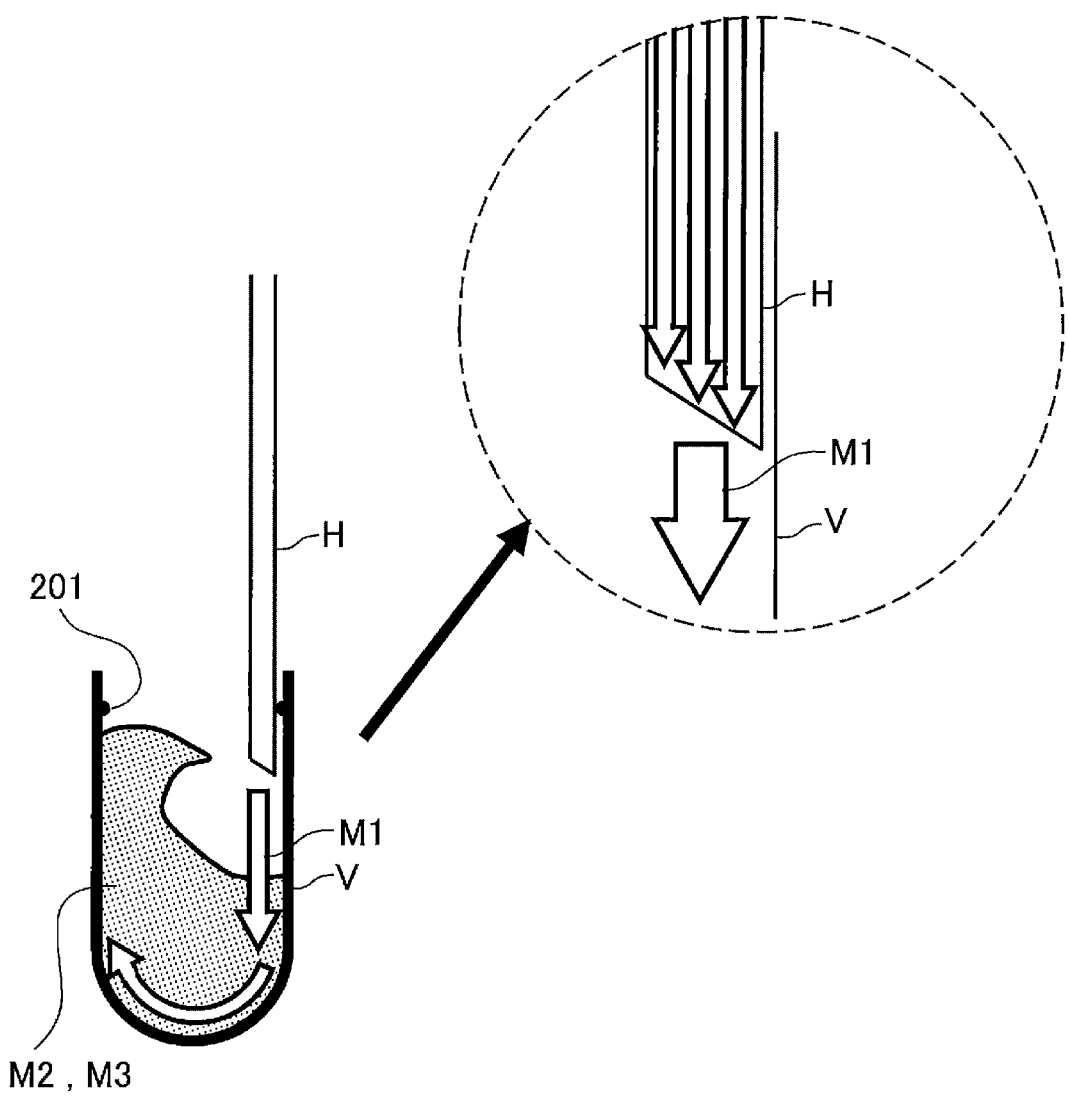

[FIG. 13]
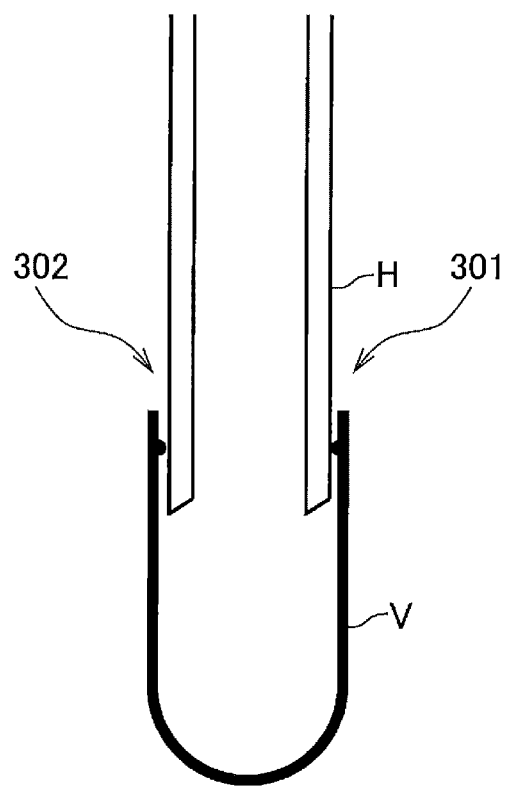

[FIG. 14]
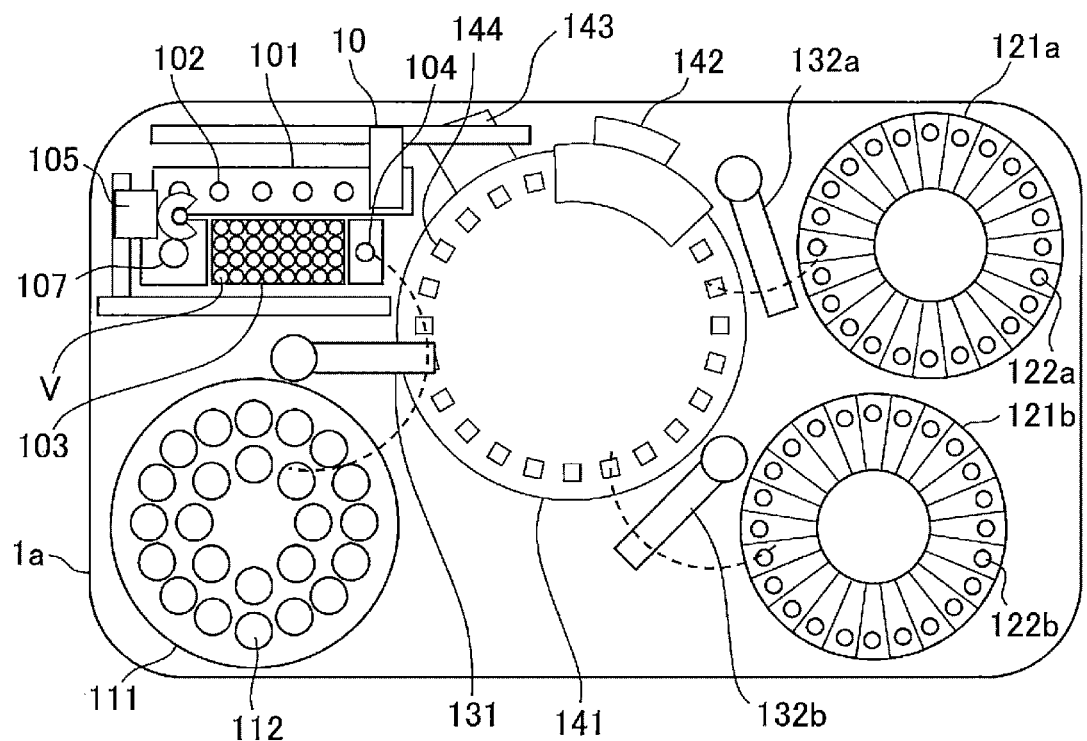
[FIG. 15]
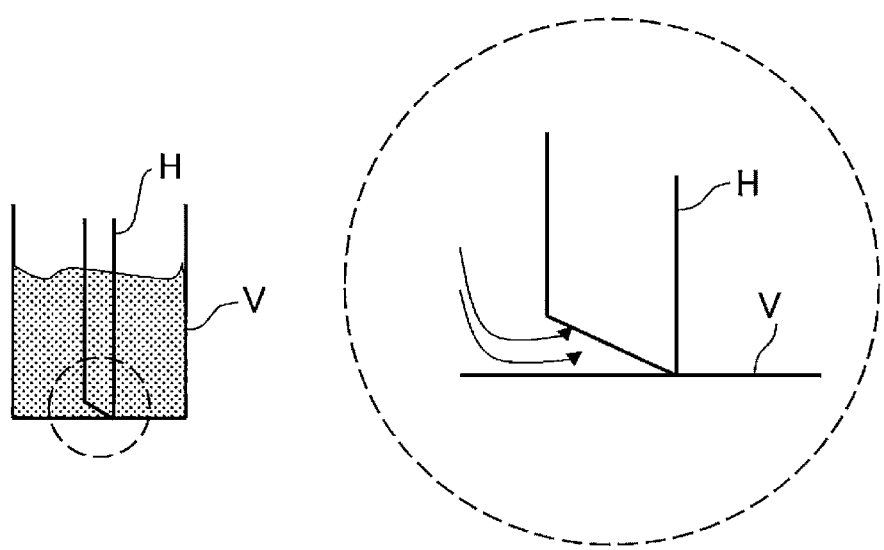

AUTOMATIC ANALYSIS DEVICE AND AUTOMATIC ANALYSIS METHOD

TECHNICAL FIELD

The present invention relates to techniques of an automatic analysis device and an analysis method by which a reaction between a specimen and a reagent is analyzed.

BACKGROUND ART

There is an automatic analysis device that analyzes the amount of a component contained in a specimen. In such an automatic analysis device, a reaction liquid in which the specimen and a reagent are mixed is irradiated with light from a light source. Then, changes in the amount of transmitted light and in the amount of scattered light, of a single or a plurality of wavelengths thus obtained, are measured. Accordingly, the amount of the component is calculated based on a relationship between the amount of light and a concentration.

There are two major analysis methods in analyzing reactions of the reaction liquid, one being colorimetric analysis in which a color reaction between a substrate and an enzyme is used, and the other being homogeneous immunoassay in which an agglutination reaction due to binding of an antigen and an antibody is used. Measurement methods such as a turbidimetric immunoassay method or a latex agglutination method are used for the homogeneous immunoassay. Further, a heterogeneous immunoassay device that performs immunoassay with higher sensitivity by using a detection technique based on chemical luminescence and electrochemical luminescence and by using a Bond/Free (B/F) separation technique is known as an automatic analysis device.

There is also an automatic analysis device that measures blood coagulation ability. In a blood vessel, blood retains flowability. However, once bleeding occurs, coagulation factors present in plasma and platelets are activated in a chain, and fibrinogens in the plasma are converted into fibrins and precipitated, thus stopping the bleeding.

As factors having such blood coagulation ability, there is an exogenous factor that coagulates blood leaking out of the blood vessel, and an endogenous factor that coagulates blood inside the blood vessel. As a measurement item regarding the blood coagulation ability (blood coagulation time), there is an exogenous blood coagulation reaction test, that is, prothrombin reaction time (PT). In addition, reaction time of thromboplastin (APTT), which is an activated component in an endogenous blood coagulation reaction, fibrinogen (Fbg) volume and the like are also measurement items regarding the blood coagulation ability.

In each of these measurement items of the blood coagulation ability, the blood coagulation ability is measured by detecting, with an optical, physical or electrical method, the fibrin precipitated by adding a reagent that initiates coagulation.

Among these methods, the method that uses an optical method includes the following method. For example, a reaction liquid, in which blood and a reagent are mixed, is irradiated with light, and then changes in intensity of scattered light or transmitted light over time due to the fibrin precipitated from the reaction liquid are measured. In this way, a time at which the fibrin starts to precipitate is calculated. The coagulation time in the blood coagulation reaction (particularly the fibrinogen volume item) is as short as several seconds. Therefore, light metering at a short interval of about 0.1 second is required, and since a reaction vessel cannot be reused through cleaning when the reaction liquid is coagulated, the reaction is performed at independent light metering ports. The reaction vessel is disposable.

When measuring the blood coagulation ability, since a start time of the coagulation reaction is short, stirring with a stirrer as in the colorimetric analysis and the homogeneous immunoassay is often not performed. Instead of stirring with the stirrer, stirring is performed at a discharge pressure at the time of discharging the specimen (blood) or the reagent. In this way, the specimen reacts with the reagent, and the change in the amount of light of the reaction liquid is measured.

The measurement of the automatic analysis device is required to be highly reproducible and highly reliable. Therefore, even when the reaction liquid is stirred at the discharge pressure, it is important to mix the entire reaction liquid uniformly and to obtain the reproducibility. When air bubbles are mixed into the reaction liquid, the change in the amount of light cannot be measured accurately and with good reproducibility due to the air bubbles.

PTL 1 discloses an automatic analysis device, "in which a control unit controls a dispensing mechanism of either a reagent dispensing device or a specimen dispensing mechanism to firstly discharge a predetermined volume of a liquid to a reaction vessel, and controls to, when the volume of the liquid in the reaction vessel is more than or less than a volume of a liquid discharged by the other dispensing mechanism, relatively lower a discharge rate of the dispensing mechanism whose volume of the liquid to be discharged is more with respect to a discharge rate of the dispensing mechanism whose volume of the liquid to be discharged is less, so as to discharge the liquid" (see abstract).

In addition, PTL 2 discloses an automatic analysis device "including a nozzle that sucks and discharges a reagent for a blood coagulation reaction, and a dispensing mechanism that is kept at a position when the reagent is discharged by the nozzle by pressing the nozzle within a range of elasticity against an inner wall of a reaction vessel" (see abstract).

PRIOR ART LITERATURE

Patent Literature

PTL 1: WO2014/097973
PTL 2: WO2015/079829

SUMMARY OF INVENTION

Technical Problem

According to the technique described in PTL 1, foaming of the reaction liquid can be reduced while the reaction of the entire reaction liquid is made uniform. Further, according to the technique described in PTL 1, since a mechanism for stirring the reaction liquid is unnecessary, simplification of the system and reduction in time required for stirring can be realized, and the processing capacity can be improved. However, when the volume of the specimen is about twice the volume of the reagent and the viscosity of the reagent is large, the discharge rate of the reagent is increased in order to improve a stirring efficiency. However, further improvements are necessary to reduce contamination.

According to the technique described in PTL 2, it is possible to realize that an air bubble is not mixed into the reaction liquid of the specimen and the reagent by dropping the reagent along an inner wall of the reaction vessel. However, further improvements are necessary to reduce contamination.

The invention has been made in view of such a background, and an object of the invention is to perform discharge in accordance with a state of a liquid substance discharged from a nozzle.

Solution to Problem

In order to solve the problems, an automatic analysis device is provided in the invention which includes: a nozzle from which a second liquid substance is discharged into a vessel storing a first liquid substance; a control unit that controls a horizontal position and orientation of the nozzle in accordance with a liquid volume of the second liquid substance and a viscosity of the second liquid substance; a dispensing unit that uses the nozzle to dispense the second liquid substance into the vessel; and a first detection unit that detects light with which a mixture of the first liquid substance and the second liquid substance is irradiated, wherein a discharge end of the nozzle is cut in an oblique direction and the control unit controls the horizontal position and orientation of the nozzle to position a short side direction of the nozzle on a wall surface side of the vessel, based on a relationship between the liquid volume of the first liquid substance in the vessel and a relationship between the viscosity of the second liquid substance and a viscosity of the first liquid substance.

Other solutions will be described below in the embodiments.

Advantageous Effect

According to the invention, discharge can be performed in accordance with a state of a liquid substance discharged from a nozzle.

BRIEF DESCRIPTION OF DRAWINGS

FIG. 1 is a diagram illustrating a configuration of an automatic analysis device Z used in a first embodiment.

FIG. 2 is a flowchart showing operations of the automatic analysis device Z.

FIG. 3 is a diagram illustrating a case where a reagent M1 is discharged when a reagent nozzle H is positioned at a center of a reaction vessel V.

FIG. 4 is a diagram illustrating a case where the reagent M1 is discharged when the reagent nozzle H is positioned on an inner wall side of the reaction vessel V.

FIG. 5 is a diagram showing an example of analysis items used in the first embodiment.

FIG. 6 is a table showing relationships between a viscosity or volume of the reagent M1 and air bubbles generation likelihood, between the viscosity or volume of the reagent M1 and a lift height of a reaction liquid M3, and between the viscosity or volume of the reagent M1 and the stirring efficiency.

FIG. 7 is a table showing relationships between a nozzle position or nozzle height and air bubble generation likelihood, between the nozzle position or nozzle height and the lift height of the reaction liquid M3, and between the nozzle position or nozzle height and the stirring efficiency.

FIG. 8 is a diagram illustrating set positions of the reagent nozzle H in item A.

FIG. 9 is a diagram illustrating set positions of the reagent nozzle H in item B.

FIG. 10 is a diagram illustrating set positions of the reagent nozzle H in item C.

FIG. 11 is a diagram illustrating a method of setting the reagent nozzle H used in a second embodiment.

FIG. 12 is a diagram illustrating a method of setting the reagent nozzle H used in a third embodiment.

FIG. 13 is a diagram illustrating a method of switching between the second embodiment and the third embodiment.

FIG. 14 is a diagram illustrating a complex analysis device 1a used in a fourth embodiment.

FIG. 15 is a diagram illustrating a state of suction in the reagent nozzle H.

DESCRIPTION OF EMBODIMENTS

Next, embodiments for implementing the invention (referred to as "embodiments") will be described in detail with reference to the drawings as appropriate.

First Embodiment (Automatic Analysis Device Z)

FIG. 1 is a diagram illustrating a configuration of an automatic analysis device Z used in the first embodiment, and FIG. 2 is a flowchart showing operations of the automatic analysis device Z.

The automatic analysis device Z will be described appropriately with reference to FIGS. 1 and 2.

The automatic analysis device Z mixes a reagent (second liquid substance) into blood (specimen (first liquid substance)) and measures a coagulation time of the blood. The automatic analysis device Z includes an analysis device 1, an interface 47, a reagent dispensing control device (control unit) 31, an Analog/Digital (A/D) converter 32, a reaction vessel transfer control device 33, and a specimen dispensing control device 34. A display device 41, a printer 42, a computer (control unit) 43, an external output medium 44, a storage device 45, and an input device 46 are connected to the interface 47. Examples of the reagent include fibrinogen and TTATP.

First, the analysis device 1 will be described.

The analysis device 1 includes a reaction vessel temperature adjustment unit 101 that is provided with a plurality of coagulation time detection units 102, and a reaction vessel supply unit 103 in which a plurality of reaction vessels (vessels) V used for measurement are stocked. The analysis device 1 further includes a reaction vessel transfer unit 105 that transfers the reaction vessels V, and a reagent dispensing device (control unit) 106 that has a reagent temperature-raising function. The analysis device 1 further includes a reaction vessel disposal unit 107, a specimen dispensing device 131, a specimen disk 111, and a reagent disk 121.

Next, general operations of blood coagulation time measurement by the automatic analysis device Z will be described.

First, the reaction vessel transfer unit 105 transfers the reaction vessel V from the reaction vessel supply unit 103 to a coagulation time specimen dispensing position 104. Then, the specimen dispensing device 131 dispenses a specimen from a specimen vessel 112 accommodated in the specimen disk 111 to the reaction vessel V at the coagulation time specimen dispensing position 104 (S1 in FIG. 2). Next, the reaction vessel V to which the specimen is dispensed is transferred by the reaction vessel transfer unit 105 to the coagulation time detection unit 102 provided in the reaction vessel temperature adjustment unit 101. Then, the specimen is heated to 37° C. by the reaction vessel temperature adjustment unit 101 provided with the coagulation time detection unit 102. Here, the reaction vessel V is disposable.

Next, a reagent dispensing device 106 sucks the reagent for the blood coagulation reaction from a reagent vessel 122. The sucked reagent is preheated to 37° C. by a reagent temperature-raising unit (not shown) provided in the reagent dispensing device 106. The preheated reagent is discharged by the reagent dispensing device 106 to the reaction vessel V. The reaction vessel V to which the specimen is dispensed is transferred to the coagulation time detection unit 102. At this time, stirring of the specimen and the reagent are implemented with the force of the reagent discharge, and blood coagulation starts.

In this way, the stirring of a reaction liquid is performed at a discharge pressure of the reagent, and accordingly a stirring mechanism is unnecessary. Therefore, simplification of the automatic analysis device Z and reduction in time for stirring can be realized.

The reaction vessel V is discarded to the reaction vessel disposal unit 107 by the reaction vessel transfer unit 105 after the blood coagulation time measurement is completed. The reagent dispensing device 106 is a pulse control type three-dimensional actuator or the like, and is capable of moving a reagent nozzle (nozzle) in three-dimensional directions.

A cleaning device 141 cleans the reagent nozzle after the reagent is discharged. As will be described below, a cleaning range of the cleaning device 141 is limited.

In FIG. 1, there are six coagulation time detection units 102 (among which one is covered by a part of the reagent dispensing device 106). That is, the coagulation time measurement is performed in parallel at six positions.

Next, a control system and a signal processing system in the automatic analysis device Z in FIG. 1 will be briefly described.

The computer 43 is connected to the reaction vessel transfer control device 33, the specimen dispensing control device 34, the reagent dispensing control device 31 and the A/D converter 32 via the interface 47.

The computer 43 sends a command to the reaction vessel transfer control device 33. The reaction vessel transfer control device 33 to which the command is send controls transfer operations of the reaction vessel V by controlling the reaction vessel transfer unit 105.

In addition, the computer 43 sends a command to the specimen dispensing control device 34. The specimen dispensing control device 34 to which the command is send controls dispensing operations of the specimen by controlling the specimen dispensing device 131.

Further, the computer 43 sends a command to the reagent dispensing control device 31. The reagent dispensing control device 31 to which the command is send controls dispensing operations of the reagent by controlling the reagent dispensing device 106.

The reagent nozzle is set at a predetermined position of the reaction vessel V through the reagent dispensing device 106 (S2 in FIG. 2). Here, the reagent nozzle is set as follows. First, information about the viscosity of the specimen and the reagent to be dispensed, the volume of the specimen, and the volume of the reagent is input into the computer 43 in advance via the input device 46. Then, the computer 43 determines the set position of the reagent nozzle based on the viscosity of the reagent, the volume of the specimen, and the volume of the reagent that are input. Then, the reagent dispensing device 106 sets the reagent nozzle at the set position determined by the computer 43.

As described above, the reagent dispensing device 106 discharges the reagent from the reagent nozzle set at a predetermined position with respect to the reaction vessel V (S3 in FIG. 2). The specimen and the reagent in the reaction vessel V are stirred by the discharge energy of the discharge.

After the stirring is finished, the reagent dispensing control device 31 controls the reagent dispensing device 106 to pull the reagent nozzle upward (S4 in FIG. 2).

Thereafter, the reagent dispensing control device 31 controls the cleaning device 141 to clean the reagent nozzle (S5 in FIG. 2). Contamination of the reagent nozzle can be prevented to some extent by this cleaning. However, the cleaning is performed only in a limited cleaning range. Since space-saving, and miniaturization of a pump accompanying reduction of cleaning water volume have been carried out, it is difficult to broaden the cleaning range.

After cleaning the reagent nozzle, the reagent dispensing control device 31 moves the reagent nozzle to the reagent dispensing device 106 and sets the reagent nozzle for the next reaction vessel V (S2 in FIG. 2).

The reaction vessel V in which the reagent and the specimen are stirred is subjected to photometry using a photometer (a first detection unit, detection unit) 142. That is, the light that is emitted from a light source (not shown) and passes through the reaction vessel V is measured, so as to measure a degree of coagulation of the reaction liquid in which the reagent and the specimen are stirred.

A photometric value measured by the photometer 142 is sent to the A/D converter 32.

Then, the photometric value converted into a digital signal by the A/D converter 32 is taken into the computer 43. The computer 43 calculates the blood coagulation time of the specimen based on the taken photometric value.

The printer 42 for printing, the storage device 45 for storing information, the external output medium 44, the input device 46 for inputting an operation command and the like, and the display device 41 for screen display are connected to the interface 47. The display device 41 is, for example, a CRT display or a liquid crystal display. The storage device 45 is, for example, a hard disk storage device or an external storage device. The storage device 45 stores information such as a password of each operator, a display level of each screen, an analysis parameter, analysis item request contents, a calibration result, and an analysis result.

The external output medium 44 is a Digital Versatile Disk (DVD), a Compact Disk (CD), or the like.

(Discharge Stirring Method)

Next, a discharge stirring method will be described with reference to FIGS. 3 and 4.

FIG. 3 is a diagram illustrating a case where a reagent M1 is discharged when a reagent nozzle H is positioned at a center of the reaction vessel V. In FIGS. 3 and 4, and FIGS. 8 to 10, a schematic top view of the reaction vessel V and the reagent nozzle H is shown at an upper side on the paper, and a schematic side sectional view of the reaction vessel V and the reagent nozzle H is shown at a lower side on the paper.

In FIGS. 3 and 4, and FIGS. 8 to 12, outlined arrows indicate flow of the reagent M1 after being discharged.

In FIG. 3, the reagent M1 is discharged from the reagent nozzle H when the reagent nozzle H is disposed horizontally at the center position of the reaction vessel V. Depending on a ratio of a volume of a specimen M2 to a volume of the reagent M1 (when the specimen M2 is less than the reagent M1), a portion of a reaction liquid M3 moves via a bottom surface of the reaction vessel V along the flow of the reagent M1. The reaction liquid M3 is a mixture of the reagent M1 and the specimen M2. Accordingly, the reaction liquid M3 is stirred. As a result, most of the reagent M1 collides with the specimen M2 and the reaction liquid M3 is stirred. Accordingly, as shown in FIG. 3, the reagent M1 is discharged from the center of the reaction vessel V. However, in this method, air bubbles are likely to generate.

In the method of FIG. 3, since the discharge energy is dispersed around the reaction vessel V, the reaction liquid M3 is difficult to lift. Therefore, in the method of FIG. 3, the reaction liquid M3 is difficult to adhere to the reagent nozzle H, and contamination to a next test is difficult to occur.

It is preferable that a protruding portion 201 is formed in an annular shape on an inner side of the reaction vessel V as shown in FIG. 3. By providing such a protruding portion 201, the reagent M1 that has moved up between the reagent nozzle H and an inner wall of the reaction vessel V due to the capillary phenomenon can be stopped by the protruding portion 201 even when the reagent nozzle H is positioned on an inner wall side of the reaction vessel V as shown in FIG. 4. The protruding portion 201 is provided on the inner side of the reaction vessel V in the following drawings, but the protruding portion 201 may be omitted.

FIG. 4 is a diagram illustrating a case where the reagent M1 is discharged when the reagent nozzle H is positioned on the inner wall side of the reaction vessel V.

In FIG. 4, the reagent M1 is discharged when the reagent nozzle H is positioned on the inner wall side of the reaction vessel V. Accordingly, most of the reagent M1 flows along the inner wall of the reaction vessel V and the reaction liquid M3 is stirred. In this example, a lower end of the reagent nozzle H is positioned lower than an upper end of the reaction vessel V.

There is less collision of the reagent M1 with the specimen M2 in the stirring method illustrated in FIG. 4 than the stirring method illustrated in FIG. 3. That is, the stirring method illustrated in FIG. 4 can reduce the generation of air bubbles better than the stirring method illustrated in FIG. 3. In the stirring method illustrated in FIG. 4, the discharge energy of the reagent M1 is likely to transfer from the inner wall to the bottom surface of the reaction vessel V. In other words, the discharge energy is concentrated on a side opposite to a discharge side. Therefore, the reaction liquid M3 is greatly lifted. In this way, in the stirring method illustrated in FIG. 4, the reaction liquid M3 is lifted so that the stirring can be performed. Therefore, the stirring efficiency of the stirring method illustrated in FIG. 4 is a higher than that of the stirring method illustrated in FIG. 3.

Meanwhile, in the stirring method illustrated in FIG. 4, the reaction liquid M3 is likely to lift as described above. That is, since the reaction liquid M3 is greatly lifted, the greatly lifted reaction liquid M3 may adhere to the reagent nozzle H, depending on the ratio of the volume of the specimen M2 to the volume of the reagent M1 and the viscosity of the reagent M1. Accordingly, contamination may occur in the next test.

Therefore, in the present embodiment, the reaction liquid M3 is prevented from adhering to the reagent nozzle H in accordance with the ratio of the volume of the specimen M2 to the volume of the reagent M1 and the viscosity of the reagent M1. Accordingly, in order to prevent the contamination to the next test, the following stirring method is provided.

(Example of Analysis Item)

FIG. 5 shows an example of analysis items used in the first embodiment. In describing FIGS. 5 to 7, FIGS. 3 and 4 are referred to as appropriate.

In FIG. 5, item names are shown in the first column. Volumes of the specimen M2 of the items are shown in the second column. Volumes of the reagent M1 of the items are shown in the third column. Viscosities of the reagent M1 are shown in the fourth column. The volumes of the specimen M2 in FIG. 5 are volumes of the specimen M2 in the reaction vessels V. The volumes of the reagent M1 are volumes of the reagent M1 to be discharged. The viscosity of the reagent M1 is the viscosity of the reagent M1 to be discharged.

When the volume of the reagent M1 is more than that of the specimen M2, the stirring efficiency is high (good). Conversely, when the volume of the reagent M1 is less than that of the specimen, the stirring efficiency is low (poor). When the viscosity of the reagent M1 is low, air bubbles are likely to generate in the reaction liquid M3. When the viscosity of the reagent M1 is low, the reaction liquid M3 is likely to lift. Here, the viscosity of the reagent M1 being high means that the viscosity of the reagent M1 is higher than that of the specimen M2. The viscosity of the reagent M1 being low means that the viscosity of the reagent M1 is equal to or lower than that of the specimen M2.

As shown in FIG. 5, in item A, the volume of the reagent M1 is more than that of the specimen M2. In item A, the viscosity of the reagent M1 is equal to or lower than that of the specimen M2.

In item B, the volume of the reagent M1 is less than that of the specimen M2. In item B, the viscosity of the reagent M1 is higher than that of the specimen M2.

In item C, the volume of the reagent M1 is less than that of the specimen M2. In item C, the viscosity of the reagent M1 is equal to or lower than that of the specimen M2.

In item D, the volume of the reagent M1 is more than that of the specimen M2. In item D, the viscosity of the reagent M1 is higher than that of the specimen M2.

For example, two kinds of reagents M1 may be dispensed into the specimen M2. Here, the two kinds of reagents M1 are referred to as a first reagent and a second reagent, respectively. The first reagent may be dispensed into the specimen M2 first, and thereafter the second reagent may be dispensed into the specimen M2+the first reagent. In this case, the specimen M2 in FIG. 5 refers to the specimen M2+the first reagent, and the reagent M1 in FIG. 5 refers to the second reagent. Further, a first reagent, a second reagent, a third reagent, and the like may be sequentially dispensed into the specimen M2. In this case, when the second reagent is dispensed, the specimen M2+the first reagent correspond to the specimen M2 in FIG. 5, and the second reagent corresponds to the reagent M1 in FIG. 5. When the third reagent is dispensed, the specimen M2+the first reagent+the second reagent correspond to the specimen M2 in FIG. 5, and the third reagent corresponds to the reagent M1 in FIG. 5.

The specimen M2 in FIG. 5 also includes a specimen M2 diluted with a diluent. That is, a liquid stored in the reaction vessel V when the reagent M1 is discharged from the reagent nozzle H corresponds to the specimen M2 in FIG. 5.

FIG. 6 is a table showing relationships between the viscosity or volume of the reagent M1 and the air bubble generation likelihood, between the viscosity or volume of the reagent M1 and the lift height of the reaction liquid M3, and between the viscosity or volume of the reagent M1 and the stirring efficiency. "More or less" of the volume of the reagent M1 is described with respect to the volume of the specimen M2. The items in FIG. 5 are listed in the lower-most row in FIG. 6.

When the viscosity of the reagent M1 is low (equal to or lower than the viscosity of the specimen M2), air bubbles are likely to generate (large), the reaction liquid M3 is likely to lift (high), and the stirring efficiency is good (good). It is not preferable that air bubbles are likely to generate.

When the viscosity of the reagent M1 is high (higher than the viscosity of the specimen M2), air bubbles are difficult to generate (small), the reaction liquid M3 is difficult to lift (low), and the stirring efficiency is poor (bad).

When the volume of the reagent M1 is less than that of the specimen M2, air bubbles are difficult to generate (small), lift of the reaction liquid M3 is low (low), and the stirring efficiency is poor (bad).

When the volume of the reagent M1 is more than that of the specimen M2, air bubbles are likely to generate (large), the lift of the reaction liquid M3 is high (high), and the stirring efficiency is good (good).

The volume of the reagent M1 has greater influence on the air bubble generation likelihood and the stirring efficiency than the viscosity of the reagent M1 does. However, the viscosity of the reagent M1 has greater influence on the lift height of the reaction liquid M3 than the volume of the reagent M1 does.

FIG. 7 is a table showing relationships between the nozzle position or nozzle height and the air bubble generation likelihood, between the nozzle position or nozzle height and the lift height of the reaction liquid M3, and between the nozzle position or nozzle height and the stirring efficiency. However, results shown in FIG. 7 are obtained in a case where the viscosity of the reagent M1 is kept the same and the volume of the reagent M1 is kept the same. Actually, the results vary depending on the viscosity of the reagent M1 and the volume of the reagent M1.

Here, the nozzle position is the position of the reagent nozzle H in a horizontal direction. The position shown in FIG. 3 is "middle", and the position shown in FIG. 4 is "end". The nozzle height "upper" means that the reagent nozzle H is set high, and the nozzle height "lower" means that the reagent nozzle H is set low.

When the nozzle position is "middle", air bubbles are likely to generate (large), the lift height is low (low), and the stirring efficiency is poor (bad).

When the nozzle position is "end", air bubbles are difficult to generate (small), the lift height is high (high), and the stirring efficiency is good (good).

When the nozzle height is "upper", air bubbles are likely to generate (large), the lift height is low (low), and the stirring efficiency is poor (bad).

When the nozzle height is "lower", air bubbles are difficult to generate (small), the lift height is high (high), and the stirring efficiency is good (good).

The reason why the lift height is high when the nozzle height is "lower" is that the reagent M1 reaches the specimen M2 at a large discharge rate.

Hereinafter, a set position of the reagent nozzle H in each of items A, B, C, and D in FIG. 5 will be described. In FIGS. 8 to 10, the same components as those in FIGS. 3 and 4 are denoted by the same reference numerals, and description thereof will be omitted.

<Item A>

FIG. 8 is a diagram illustrating set positions of the reagent nozzle H in item A.

In item A of FIG. 5, the volume of the reagent M1 is more than that of the specimen M2, and the viscosity of the reagent M1 is low. That is, in item A, the stirring efficiency is high and the reaction liquid M3 is likely to lift (high), as shown in the table of FIG. 6.

Therefore, as shown on the left part of FIG. 8, when reagent M1 is discharged with the reagent nozzle H positioned on the inner wall side of the reaction vessel V, the reaction liquid M3 is likely to lift. For this reason, the reaction liquid M3 may adhere to the reagent nozzle H. Therefore, contamination may occur in the next test.

Therefore, as shown in the right part of FIG. 8, the position of the reagent nozzle H is controlled so that the reagent nozzle H discharges the reagent M1 at the center position of the reaction vessel V. Accordingly, as shown in the table of FIG. 7, the lift of the reaction liquid M3 is reduced. As a result, the reaction liquid M3 can be prevented from adhering to the reagent nozzle H. Accordingly, contamination to the next test can be prevented.

When a method illustrated on the right part of FIG. 8 is used, the reagent M1 is discharged at a center position of the reaction liquid M3. For this reason, as shown in the table of FIG. 7, the stirring efficiency is poor. However, as shown in FIG. 5, in item A, the conditions are that the volume of the reagent M1 is more than the volume of the specimen M2, and that the viscosity of the reagent M1 is low. As shown in the table of FIG. 6, the stirring efficiency is high under such conditions. Therefore, when the reagent M1 is discharged at the center position of the reaction vessel V, it is possible to obtain sufficient stirring efficiency even when prevention of contamination to the next test is prioritized.

When the volume of the reagent M1 is more than that of the specimen M2 in the conditions of item A, the collision of the reagent M1 with the specimen M2 is increased, and the generation of air bubbles is increased as shown in the table of FIG. 6. In addition, when the nozzle position is at the center of the reaction vessel V, air bubbles are likely to generate as shown in FIG. 7. However, as described above, the results shown in the table of FIG. 7 vary depending on the actual volume of the reagent M1 and the viscosity of the reagent M1.

As shown on the right part of FIG. 8, when the reagent M1 is discharged from the center position of the reaction vessel V, since the volume of the reagent M1 is more than that of the specimen M2, the stirring can be performed through the bottom surface of the reaction vessel V. Specifically, since the volume of the specimen M2 is less than that of the reagent M1, the discharged reagent M1 reaches the bottom surface of the reaction vessel V. Then, the reagent M1 flows along the bottom surface of the reaction vessel V. Therefore, there is little collision between the reagent M1 and the specimen M2. Accordingly, the generation of air bubbles can be reduced in this case as compared with a case where the volume of the reagent M1 is more than that of the specimen M2.

The discharge rate of the reagent M1 and the height at which the reagent M1 is discharged also contribute to the generation of air bubbles. For this reason, depending on a relationship with the stirring efficiency, the discharge rate of the reagent M1 can be lowered to an extent that the analysis is not practically influenced, and the height at which the reagent M1 is discharged can be lowered to an extent that the reaction liquid M3 does not adhere to the reagent nozzle H. In this way, it is possible to reduce foaming (generation of air bubbles) of the reaction liquid M3 and to maintain the stirring efficiency under the conditions of item A.

Accordingly, data reproducibility can be improved, and contamination to the next test can be prevented.

A broken line L1 in FIG. 8 will be described later.

<Item B>

FIG. 9 is a diagram illustrating set positions of the reagent nozzle H in item B.

In item B of FIG. 5, the volume of the reagent M1 is less than that of the specimen M2, and the viscosity of the reagent M1 is high. That is, as shown in the table of FIG. 6, the stirring efficiency is low (poor) and the reaction liquid M3 is difficult to lift (low).

Under such a condition that the reaction liquid M3 is difficult to lift, the reaction liquid M3 is difficult to adhere to the reagent nozzle H even when the reagent M1 is discharged with the reagent nozzle H positioned on the inner wall side of the reaction vessel V, as shown on the left part of FIG. 9. In this way, in item B, the influence of contamination to the next test is relatively low even when the reagent M1 is discharged with the reagent nozzle H positioned on the inner wall side of the reaction vessel V.

However, under the conditions of item B, since the volume of the reagent M1 is less than that of the specimen M2, the stirring efficiency is low (bad) as shown in the table of FIG. 6. For this reason, it is necessary to improve the stirring efficiency.

Therefore, as shown on the right part of FIG. 9, when the reagent nozzle H is positioned on the inner wall side of the reaction vessel V, the height of the reagent nozzle H is lowered to a height lower than a reference position L1 and to a height at which the lifted reaction liquid M3 does not adhere to the reagent nozzle H. Here, the reference position L1 indicates the height of the broken line L1 in FIG. 8.

As shown in the table of FIG. 7, when the height of the reagent nozzle H is lowered, the stirring efficiency can be improved.

In item B, depending on a relationship with the stirring efficiency as in item A, the discharge rate of the reagent M1 can be reduced to an extent that the analysis is not practically influenced. In this way, the generation of air bubbles in the reaction liquid M3 can be further reduced under the conditions of item B. As described above, when the height of the reagent nozzle H is lowered, the stirring efficiency can be improved. Accordingly, the data reproducibility can be improved, and contamination to the next test can be prevented.

It is not necessary to broaden the cleaning range of the reagent nozzle H by preventing the reaction liquid M3 from adhering to the reagent nozzle H.

<Item C>

FIG. 10 is a diagram illustrating set positions of the reagent nozzle H in item C.

As shown in the table of FIG. 6, in item C, all conditions are conflicting. That is, air bubbles are likely to generate (large) according to the viscosity of the reagent M1, but bubbles are difficult to generate according to the volume of the reagent M1 (small). Similarly, the lift height of the reaction liquid M3 is high (high) according to the viscosity of the reagent M1, but the lift height is low (low) according to the volume of the reagent M1. The stirring efficiency is high (good) according to the viscosity of the reagent M1, but the stirring efficiency is low (bad) according to the volume of the reagent M1.

However, as described above, the volume of the reagent M1 has greater influence on the air bubble generation likelihood and the stirring efficiency, and the viscosity thereof has greater influence on the lift height of the reaction liquid M3.

Therefore, in item C, there are problems that the stirring efficiency is low and that the lift height of the reaction liquid M3 is high.

In the conditions of item C, since the viscosity of the reagent M1 is low, the reaction liquid M3 is likely to lift (high) as shown in the table of FIG. 6. However, since the volume of the reagent M1 in item C is less than in item A, that is, the volume of the reagent M1 has smaller influence in item C than in item A, the lift of the reaction liquid M3 in item C is lower than in item A. Therefore, the reagent nozzle H is set on the inner wall side of the reaction vessel V in consideration of the stirring efficiency.

As described above, the lift of the reaction liquid M3 is high in item C although not as high as in item A. Therefore, when the reagent M1 is discharged at a height similar to that on the left part or on the right part of FIG. 9, the reaction liquid M3 may adhere to the reagent nozzle H as shown on the left part of FIG. 10. That is, the possibility of occurrence of contamination to the next test is relatively high. Therefore, as shown the right part of FIG. 10, the height of the reagent nozzle H is set higher than the reference position L1 with the reagent nozzle H positioned on the inner wall side of the reaction vessel V. Here, the reference position L1 indicates the height of the broken line L1 in FIG. 8. Specifically, the reagent nozzle H is set high to a height at which the lifted reaction liquid M3 does not adhere. In this way, the reaction liquid M3 is difficult to lift (low) as shown in the table of FIG. 7. That is, adhesion of the reaction liquid M3 to the reagent nozzle H due to the lift of the reaction liquid M3 can be avoided.

In particular, it is not necessary to broaden the cleaning range of the reagent nozzle H.

When the height of the reagent nozzle H is increased (upward), air bubbles are likely to generate and the stirring efficiency is lowered, as shown in the table of FIG. 7. However, since the volume of the reagent M1 has greater influence on the air bubble generation likelihood, air bubbles are difficult to generate in item C as shown in the table of FIG. 7. Therefore, air bubbles are difficult to generate even when the reagent nozzle H is set high.

As shown in the table of FIG. 6, the stirring efficiency is low under the conditions of item C. Here, when the height of the reagent nozzle H is increased, the stirring efficiency is lowered as shown in the table of FIG. 7. However, in this case, the prevention of contamination is prioritized. This is because contamination has great influence on results of the next test. However, in item C, since the reagent nozzle H is set on the inner wall side of the reaction vessel V, the stirring efficiency is improved accordingly (see FIG. 7). Accordingly, stirring efficiency can be prevented from lowering to some extent.

<Item D>

As shown in the table of FIG. 6, all the conditions are conflicting in item D. That is, air bubbles are difficult to generate (small) according to the viscosity of the reagent M1, but bubbles are likely to generate according to the volume of the reagent M1 (large). Similarly, the lift height of the reaction liquid M3 is low (low) according to the viscosity of the reagent M1, but the lift height is high (high) according to the volume of the reagent M1. The stirring efficiency is low (bad) according to the viscosity of the reagent M1, but the stirring efficiency is good (good) according to the volume of the reagent M1.

However, as described above, the volume of the reagent M1 has greater influence on the air bubble generation likelihood and the stirring efficiency, and the viscosity thereof has greater influence on the lift height of the reaction liquid M3.

Therefore, in item D, air bubbles are likely to generate and the stirring efficiency is high, as shown in the table of FIG. 7. Since the viscosity of the reagent M1 is high, the lift height of the reaction liquid M3 is low. That is, compared with items A to C, item D has favorable conditions other than the fact that air bubbles are likely to generate.

Therefore, in the case of item D, when the nozzle position is set to the position as on the left part of FIG. 8, the generation of air bubbles is suppressed.

It should be noted that the computer 43 determines the relationship between the reagent M1 and the specimen M2 corresponds to which one of items A to D in FIG. 5. Here, the information such as the volume of the reagent M1, the volume of the specimen M2 and the viscosity of the reagent M1 is input via, for example, the input device 46 (see FIG. 1).

When the reagent nozzle H is positioned on the inner wall side of the reaction vessel V, the reagent nozzle H may be set at any position of the reaction vessel V. That is, for example, the reagent nozzle H is set in a forward direction of an X axis on the upper part of FIG. 4, and alternatively the reagent nozzle H may be set at any position defined by XY axes as long as the reagent nozzle H is on the inner wall side of the reaction vessel V.

The automatic analysis device Z performs discharge stirring with the reagent M1 to stir the specimen M2 and the reagent M1, for blood coagulation or the like, and measures the time the coagulation reaction of the reaction liquid M3 takes by optical detection. In order to improve the data reproducibility, such an automatic analysis device Z needs to reduce foaming (generation of air bubbles) in the reaction liquid M3, improve the stirring efficiency, and prevent contamination to the next test.

In the first embodiment, the reagent dispensing device 106 controls the horizontal position of the reagent nozzle H in accordance with the viscosity and the volume of the reagent M1. In this way, it is possible to discharge the reagent M1 in accordance with the state of the reagent M1.

According to the first embodiment, when the volume of the reagent M1 is more than that of the specimen M2 and the viscosity of the reagent M1 is low, the reagent dispensing control device 31 positions the horizontal position of the reagent nozzle H at the center of the reaction vessel V. That is, the horizontal position of the reagent nozzle H is set at the center of the reaction container V under a condition that the reaction liquid M3 is likely to lift. As shown in FIG. 7, when the reagent nozzle H is set at the center of the reaction vessel V, the reaction liquid M3 is difficult to lift. In this way, the reaction liquid M3 can be prevented from adhering to the reagent nozzle H. Therefore, contamination to the next test can be prevented.

According to the first embodiment, when the volume of the reagent M1 is less than that of the specimen M2 or the viscosity of the reagent M1 is high, the reagent dispensing control device 31 positions the horizontal position of the reagent nozzle H on the inner wall side of the reaction vessel V. That is, under the condition that the reaction liquid M3 is difficult to lift, air bubbles are difficult to generate, and the reagent nozzle H is set on the inner wall side of the reaction vessel V where high stirring efficiency is realized. In this way, the reaction liquid M3 can be prevented from adhering to the reagent nozzle H, the generation of the air bubbles can be reduced, and the stirring efficiency can be improved.

According to the first embodiment, when the volume of the reagent M1 is less than that of the specimen M2, the reagent dispensing control device 31 controls the height of the reagent nozzle H in accordance with the volume of the reagent M1 and the viscosity of the reagent M1. In this way, the generation of air bubbles and the stirring efficiency can be controlled.

When the volume of the reagent M1 is less than that of the specimen M2 and the viscosity of the reagent M1 is high, the reagent dispensing control device 31 lowers the height of the reagent nozzle H to a height at which the reaction liquid M3 does not adhere to the reagent nozzle H. In this way, the stirring efficiency can be improved.

When the volume of the reagent M1 is less than that of the specimen M2 and the viscosity of the reagent M1 is low, the reagent dispensing control device 31 increases the height of the reagent nozzle H to a height at which the reaction liquid M3 does not adhere to the reagent nozzle H. In this way, contamination can be prevented.

The protruding portion 201 is provided in an annular shape on the inner wall of the reaction vessel V. In this way, the reagent M1 can be stopped by the protruding portion 201 from rising through a gap between the reaction vessel V and the reagent nozzle H due to the capillary phenomenon.

In addition, the lift height of the reaction liquid M3 can be reduced by providing the protruding portion 201. The reason for this is as follows.

When the reagent M1 is discharged, with the reagent nozzle H being in close contact with the inner wall of the reaction vessel V and without providing the protruding portion 201, the discharged reagent M1 moves along the bottom and the inner wall of the reaction vessel V. For this reason, although there is slight loss of the discharge energy due to friction with the inner wall of the reaction vessel V, the discharged reagent M1 reaches the side opposite to the discharge side with a little loss of the discharge energy. For this reason, the reaction liquid M3 is greatly lifted on the side opposite to the discharge side.

In contrast, when the protruding portion 201 is provided, the reagent nozzle H is set slightly away from the inner wall of the reaction vessel V. When the reagent M1 is discharged with the reagent nozzle H set slightly away from the inner wall of the reaction vessel V, most of the reagent M1 reaches the bottom of the reaction vessel V without flowing along the inner wall of the reaction vessel V. Therefore, most of the reagent M1 collides with the bottom of the reaction vessel V at a position slightly away from the inner wall of the reaction vessel V, and thereafter reaches the side opposite to the discharge side along the bottom of the reaction vessel V. Here, when the discharged reagent M1 collides with the bottom of the reaction vessel V, there is a loss of the discharge energy. Therefore, the kinetic energy of the reagent M1 that has reached the side opposite to the discharge side is less than the kinetic energy in a case where the reagent M1 is discharged with the reagent nozzle H being in close contact with the inner wall of the reaction vessel V. That is, the lift is lower than in a case where the reagent M1 is discharged with the reagent nozzle H being in close contact with the inner wall of the reaction vessel V.

Since there is no loss of energy caused by the friction between the discharged reagent M1 and the inner wall of the reaction vessel V by providing the protruding portion 201, the stirring efficiency can be improved.

Further, an overflow due to the lift of the reaction liquid M3 can be prevented by providing the protruding portion 201.

As shown in FIG. 1, the automatic analysis device Z that measures blood coagulation while preventing contamination can be realized, with the specimen M2 being blood and the reagent M1 being a reagent for coagulating the blood.

According to the first embodiment, the existing automatic analysis device Z can be used by merely changing a program that controls the position of the reagent nozzle H. Accordingly, the cost can be reduced.

Second Embodiment

FIG. 11 is a diagram illustrating a method of setting the reagent nozzle H used in a second embodiment.

As shown in FIG. 11, the reagent nozzle H whose tip is in an oblique shape is set on the inner wall side of the reaction vessel V in the second embodiment. The reagent nozzle H is set with a short side direction of the reagent nozzle H directed toward the inner wall of the reaction vessel V.

When the reagent M1 is discharged with the short side direction of the reagent nozzle H directed toward the inner wall of the reaction vessel V, the reagent M1 flowing on a short side direction side of the reagent nozzle H flows along the inner wall of the reaction vessel V due to the surface tension with the inner wall of the reaction vessel V, as shown in a broken line circle in FIG. 11.

Details are as follows. The inner wall of the reaction vessel V and the reagent nozzle H are slightly separated from each other by the protruding portion 201 provided in a storage vessel. However, a reagent M1$a$, flowing along the innermost wall side of the reaction vessel V among the reagent M1 discharged from the reagent nozzle H, reaches the inner wall of the reaction vessel V beyond a separation portion generated by the protruding portion 201 due to the surface tension of the reagent M1. Thereafter, the reagent M1$a$ reaching the inner wall of the reaction vessel V flows along the inner wall.

Then, a reagent M1$b$ flowing in the middle of the reagent nozzle H also flows along the inner wall of the reaction vessel V along the reagent M1$a$ flowing on the inner wall side of the reaction vessel V.

In the reagent nozzle H, a reagent M1$c$ flowing on a side opposite to the inner wall side of the reaction vessel V also flows along the inner wall of the reaction vessel V along the reagent M1$b$ flowing in the middle of the reagent nozzle H.

As a result, the reagent M1 discharged from the reagent nozzle H flows along the inner wall of the reaction vessel V.

In this way, the stirring can be performed with the reagent M1 flowing along the inner wall of the reaction vessel V. Since the kinetic energy of the reagent M1 is reduced due to the friction or the like with the inner wall of the reaction vessel V when flowing along the inner wall of the reaction vessel V, a rate at which the reagent M1 collides with the specimen M2 can be reduced. Accordingly, the generation of air bubbles in the reaction liquid M3 and the lift of the reaction liquid M3 can be reduced.

Third Embodiment

FIG. 12 is a diagram illustrating a method of setting the reagent nozzle H used in a third embodiment.

As shown in FIG. 12, the reagent nozzle H whose tip is in an oblique shape is set on the inner wall side of the reaction vessel V in the third embodiment. The reagent nozzle H is set with a long side direction of the reagent nozzle H directed toward the inner wall of the reaction vessel V.

When a reagent M1 is discharged with the long side direction of the reagent nozzle H directed toward the inner wall of the reaction vessel V, the stirring can be performed without the reagent M1 flowing along the inner wall of the reaction vessel V as shown in the broken line circle in FIG. 12, contrary to that in the second embodiment (FIG. 11).

For this reason, the reagent M1 is directly discharged toward the specimen M2. That is, the reagent M1 collides with the specimen M2 without reducing the kinetic energy of the reagent M1 as in the second embodiment. Therefore, the stirring efficiency can be improved.

[Switching Between Second Embodiment and Third Embodiment]

FIG. 13 is a diagram illustrating a method of switching between the second embodiment and the third embodiment.

In FIG. 13, when the reagent nozzle H is positioned at a position indicated by a reference numeral 301, the reagent nozzle H is in the form of the second embodiment. That is, the short side direction of the reagent nozzle H is directed toward the inner wall side of the reaction vessel V.

A reference numeral 302 indicates that the reagent nozzle H is positioned on a side opposite to the position 301 of the reaction vessel V. At this time, the short side direction and the long side direction of the reagent nozzle H are directed in a direction same as that indicated by the reference numeral 301. That is, when the reagent nozzle H is positioned at a position indicated by the reference numeral 302, the reagent nozzle H is in the form of the third embodiment. In other words, the long side direction of the reagent nozzle H is directed toward the inner wall side of the reaction vessel V.

Whether the reagent nozzle H is set at the position indicated by the reference numeral 301 or set at the position indicated by the reference numeral 302 depends on the volume and the viscosity of the reagent M1.

Specifically, the computer 43 performs determination under the following conditions, and determines the set position of the nozzle H.

(Condition 1) When the viscosity of the reagent M1 is low and the volume of the reagent M1 is more than that of the specimen M2: the reagent nozzle H is set at the position 301.

Under such conditions, as shown in FIG. 6, although the stirring efficiency is high, air bubbles are likely to generate and the lift is likely to occur. In this case, as indicated by the reference numeral 301, the short side direction of the reagent nozzle H is directed toward the inner wall side of the reaction vessel V. As described above, with such a setting method, the generation of air bubbles in the reaction liquid M3 and the lift of the reaction liquid M3 can be reduced.

(Condition 2) When the viscosity of the reagent M1 is high and the volume of the reagent M1 is less than that of the specimen M2: the reagent nozzle H is set at the position 302.

Under such conditions, as shown in FIG. 6, although air bubbles are difficult to generate and the lift is difficult to occur, the stirring efficiency is low. In this case, as indicated by the reference numeral 302, the long side direction of the reagent nozzle H is directed toward the inner wall side of the reaction vessel V. As described above, with such a setting method, the reagent M1 collides with the specimen M2 without reducing the kinetic energy of the reagent M1. Therefore, the stirring efficiency can be improved.

When the measurement result is greatly influenced due to mixing of a small volume of impurities, the reagent nozzle H may be set at the position indicated by the reference numeral 301. In this way, the reagent M1 can collide with the specimen M2 with the kinetic energy thereof being reduced. In this way, the mixing can be performed stably. The reagent M1 collides with the specimen M2 with the kinetic energy thereof being reduced, and accordingly impurities can be prevented from being mixed in during the collision.

Here, whether the short side direction or the long side direction of the reagent nozzle H is directed toward the inner wall side is selected in accordance with the set position of the reagent nozzle H with respect to the reaction vessel V. However, the present invention is not limited thereto, and the reagent dispensing device 106 changes the direction of the reagent nozzle, so as to select whether the short side direction or the long side direction of the reagent nozzle H is directed toward the inner wall side.

Fourth Embodiment

FIG. 14 is a diagram illustrating a complex analysis device 1a used in a fourth embodiment.

The complex analysis device 1a shown in FIG. 14 is a complex analysis device having a biochemical analysis function added to the analysis device 1 shown in FIG. 1.

The complex analysis device 1a shown in FIG. 14 includes a reaction disk 141, a first reagent sampling device 132a and a second reagent sampling device 132b, in addition to the configuration of the analysis device 1 that measures the blood coagulation time in FIG. 1. The complex analysis device 1a further includes a first reagent disk 121a, a second reagent disk 121b, and a reaction cell cleaning device 142. The reaction disk 141 of the complex analysis device 1a includes a photometer (a second detection unit) 143 and a reaction cell 144.

The complex analysis device 1a performs biochemical analysis and blood coagulation time measurement in the following procedure.

First, a reagent is placed on the first reagent disk 121a and the second reagent disk 121b. Then, the first reagent sampling device 132a and the second reagent sampling device 132b suck a reagent for blood coagulation and discharge the reagent for blood coagulation into the reaction cell 144.

Specifically, a first reagent (a third liquid substance) stored in a first reagent vessel 122a of the first reagent disk 121a is discharged to the reaction cell 144 by the first reagent sampling device 132a. Thereafter, a second reagent (a fourth liquid substance) stored in a second reagent vessel 122b of the second reagent disk 121b is discharged to the reaction cell 144 by the second reagent sampling device 132b. Then, a reaction (a biochemical reaction) between the first reagent and the second reagent in the reaction cell 144 is measured by the photometer 143.

When the measurement of the reaction between the first reagent and the second reagent is completed, a reaction liquid of the first reagent and the second reagent is discharged to the reaction vessel V (specimen injected) in the coagulation time detection unit 102 by the same procedure as in FIG. 2.

After dispensing of the first reagent and the second reagent is completed, the reaction cell 144 is cleaned by the reaction cell cleaning device 142.

A temperature adjustment unit (not shown) is provided on the reaction disk 141, and the reaction liquid of the first reagent and the second reagent is heated in the reaction cell 144.

In the blood coagulation measurement, it is desirable that the temperature of the reagent is adjusted to around 37° C. Since the temperature of the reaction cell 144 is kept around 37° C., the reagent can be preheated to around 37° C. The reagent preheated to around 37° C. in the reaction cell 144 is sucked by the reagent dispensing device 106. Thereafter, the automatic analysis device Z shown in FIG. 1 performs the blood coagulation measurement by the same procedure as in FIG. 2. Therefore, since the reagent (the reaction liquid of the first reagent and the second reagent) dispensed into the specimen is heated in advance, the preheating time can be reduced.

In this way, the complex analysis device 1a that performs biochemical analysis and blood coagulation analysis can be realized.

When a tip shape of the reagent nozzle H is an oblique shape, a gap is formed between a bottom surface of the reaction cell 144 and the reagent nozzle H as shown in FIG. 15, and the reagent can be sucked efficiently as shown in a broken line circle in FIG. 15. As a result, a dead volume of the reagent can be reduced.

The invention is not limited to the above-described embodiments, and includes various modifications. For example, the above-described embodiments have been described in detail for easy understanding of the invention, and are not necessarily limited to those having all the described configurations. Apart of the configuration of one embodiment can be replaced with the configuration of another embodiment, and the configuration of another embodiment can also be added to the configuration of one embodiment. A part of the configuration of each embodiment may be combined with another configuration, omitted, or replaced with another configuration.

Some or all of the above-described configurations, functions, the storage device 45, and the like may be realized by hardware, for example, by designing an integrated circuit. As shown in FIG. 1, the above-described configurations, functions, and the like may be realized by a processor such as a CPU in the computer 43 with software through interpreting and executing a program for realizing the functions. Information of programs, tables, files, and the like for implementing each function can be stored in a recording device such as the storage device 45 and a Solid State Drive (SSD), or a recording medium such as an Integrated Circuit (IC) card, a Secure Digital (SD) card, or a Digital Versatile Disc (DVD).

In each embodiment, control lines and information lines, considered to be necessary for description, are shown, and not all the control lines and information lines are necessarily shown in the product. In practice, almost all the configurations may be considered to be connected to each other.

REFERENCE SIGN LIST 1 analysis device
1a complex analysis device
31 reagent dispensing control device (control unit)
33 reaction vessel transfer control device
34 specimen dispensing control device
43 computer (control unit)
101 reaction vessel temperature adjustment unit
102 coagulation time detection unit
103 reaction vessel supply unit
104 specimen dispensing position
105 reaction vessel transfer unit
106 reagent dispensing device (control unit)
111 specimen disk
121 reagent disk
121a first reagent disk
121b second reagent disk
122a first reagent vessel (third liquid substance contained)
122b second reagent vessel (fourth liquid substance contained)
131 specimen dispensing device
132a first reagent sampling device
132b second reagent sampling device
141 cleaning device
142, 143 photometer (first detection unit, detection unit)

The invention claimed is:

1. An automatic analysis device, comprising:
a nozzle from which a second liquid substance is discharged into a vessel storing a first liquid substance;

a control processor configured to control a horizontal position and orientation of the nozzle in accordance with a liquid volume of the second liquid substance and a viscosity of the second liquid substance;

a dispensing unit that uses the nozzle to dispense the second liquid substance into the vessel; and a first detection unit that detects light with which a mixture of the first liquid substance and the second liquid substance is irradiated, wherein a discharge end of the nozzle is cut in an oblique direction so as to control a direction of the second liquid substance upon discharge from the discharge end of the nozzle being positioned at one of a short side of said discharge nozzle and a long side of said discharge nozzle with respect to an inner wall of the vessel, such that when the short side of the nozzle is disposed toward the inner wall of the reaction vessel a first portion of the second liquid substance flows at said short side of the nozzle as the first portion exits the nozzle nearest to the inner wall of the reaction vessel and contacts with said inner wall at a first location spaced apart from said discharge end of said nozzle, a second portion of the second liquid substance flows along said first portion as the second portion exits the nozzle and contacts with said inner wall at a second location spaced apart from said discharge end of said nozzle, said second location being farther from said discharge end of said nozzle than said first location, and a third portion of the second liquid substance flows at said short side of the nozzle along said second portion as the third portion exits the nozzle farthest from the inner wall of the reaction vessel and contacts with said inner wall at a third location spaced apart from said discharge end of said nozzle, said third location being farther from said discharge end of said nozzle than said second location, the vessel comprises an annular protruding portion disposed on the inner wall of the vessel, the control processor is configured to control the horizontal position and orientation of the nozzle to position the short side of the discharge nozzle on the inner wall surface side of the vessel so that the nozzle in contact with the protruding portion and is set a distance away from the inner wall surface of the vessel so as to cause a loss of discharge energy of the second liquid substance colliding with a bottom of the vessel after exiting the nozzle, based on a relationship between the liquid volume of the second liquid substance to be discharged and a liquid volume of the first liquid substance in the vessel and a relationship between the viscosity of the second liquid substance and a viscosity of the first liquid substance, and each of the first, second, and third portions of the second liquid substance flow along the inner wall after contacting with the inner wall at said first location, said second location, and said third location, respectively, to achieve stirring of the second liquid substance at a friction-caused reduced rate to prevent generation of bubbles caused by the second liquid substance colliding with the first liquid substance.

2. The automatic analysis device according to claim 1, wherein
the control processor determines whether to position the short side of the nozzle on the wall surface side of the vessel or to position the long side of the nozzle on the wall surface side of the vessel, based on the relationship between the liquid volume of the second liquid substance to be discharged and the liquid volume of the first liquid substance in the vessel and the relationship between the viscosity of the second liquid substance and the viscosity of the first liquid substance.

3. The automatic analysis device according to claim 1, wherein
the control is further configured to control a height of the nozzle based on a relationship between the liquid volume of the second liquid substance to be discharged and the liquid volume of the first liquid substance in the vessel and the relationship between the viscosity of the second liquid substance and the viscosity of the first liquid substance.

4. The automatic analysis device according to claim 1, wherein
the control processor is further configured to control a height of the nozzle so that the nozzle is lowered to a height at which the mixture of the first liquid substance and the second liquid substance does not adhere to the nozzle, when the liquid volume of the second liquid substance to be discharged is less than the liquid volume of the first liquid substance in the vessel, and the viscosity of the second liquid substance to be discharged is higher than the viscosity of the first liquid substance in the vessel.

5. The automatic analysis device according to claim 1, wherein
the control processor is further configured to control a height of the nozzle so that the nozzle is raised to a height at which the mixture of the first liquid substance and the second liquid substance does not adhere to the nozzle, when the volume of the second liquid substance to be discharged is less than the liquid volume of the first liquid substance in the vessel, and the viscosity of the second liquid substance to be discharged is equal to or lower than the viscosity of the first liquid substance in the vessel.

6. The automatic analysis device according to claim 1, wherein
the first liquid substance is blood, and
the second liquid substance is a substance that coagulates the blood.

7. The automatic analysis device according to claim 1, further comprising:
a second detection unit that measures a chemical reaction of a mixture obtained by mixing a third liquid substance and a fourth liquid substance in a vessel different from the vessel, wherein
the first liquid substance is the mixture of the third liquid substance and the fourth liquid substance.

8. An analysis method for an automatic analysis device including:
a nozzle from which a second liquid substance is discharged into a vessel storing a first liquid substance;
a control processor configured to control a horizontal position and orientation of the nozzle in accordance with a liquid volume of the second liquid substance and a viscosity of the second liquid substance;
a dispensing unit that uses the nozzle to dispense the second liquid substance into the vessel; and
a detection unit that detects light with which a mixture of the first liquid substance and the second liquid substance is irradiated, wherein
a discharge end of the nozzle is cut in an oblique direction so as to control a direction of the second liquid substance upon discharge from the discharge end of the nozzle being positioned at one of a short side of said discharge nozzle and a long side of said discharge nozzle with respect to an inner wall of the vessel,
the vessel comprises an annular protruding portion disposed on an inner wall of the vessel, and
the analysis method comprising:
controlling, by the control processor, the horizontal position and orientation of the nozzle to position a short side of the nozzle on the inner wall surface side of the vessel so that the nozzle in contact with the protruding portion is set a distance away from the inner wall surface of the vessel so as to cause a loss of discharge energy of the second liquid substance by colliding with a bottom of the vessel after exiting the nozzle, based on a relationship between the liquid volume of the second liquid substance to be discharged and a liquid volume of the first liquid substance in the vessel and a relationship between the viscosity of the second liquid substance and a viscosity of the first liquid substance;
controlling, by the control processor, the horizontal position and orientation of the nozzle to position the short side of the nozzle on the inner wall surface side of the vessel so that
 a first portion of the second liquid substance flows at said short side of the nozzle as the first portion exits the nozzle nearest to the inner wall of the reaction vessel and contacts with said inner wall at a first location spaced apart from said discharge end of said nozzle,
 a second portion of the second liquid substance flows along said first portion as the second portion exits the nozzle and contacts with said inner wall at a second location spaced apart from said discharge end of said nozzle, said second location being farther from said discharge end of said nozzle than said first location, and
 a third portion of the second liquid substance flows at said short side of the nozzle along said second portion as the third portion exits the nozzle farthest from the inner wall of the reaction vessel and contacts with said inner wall at a third location spaced apart from said discharge end of said nozzle, said third location being farther from said discharge end of said nozzle than said second location; and
controlling, by the control processor, the horizontal position and orientation of the nozzle to position the short side of the nozzle on the inner wall surface side of the vessel to cause each of the first, second, and third portions of the second liquid substance to flow along the inner wall after contacting with the inner wall at said first location, said second location, and said third location, respectively, to achieve stirring of the second liquid substance at a friction-caused reduced rate to prevent generation of bubbles caused by the second liquid substance colliding with the first liquid substance.

9. The automatic analysis device according to claim 2, wherein
the control processor is further configured to control the horizontal position and orientation of the nozzle to position the long side of the nozzle on the wall surface side of the vessel, when the liquid volume of the second liquid substance to be discharged is less than the volume of the first liquid substance in the vessel and the viscosity of the second liquid substance is higher than the viscosity of the first liquid substance.

\* \* \* \* \*